United States Patent
Watkins

(10) Patent No.: US 12,141,324 B2
(45) Date of Patent: *Nov. 12, 2024

(54) SYSTEMS AND METHODS FOR TOKENIZATION OF PERSONALLY IDENTIFIABLE INFORMATION (PII) AND PERSONAL HEALTH INFORMATION (PHI)

(71) Applicant: MASTERCARD INTERNATIONAL INCORPORATED, Purchase, NY (US)

(72) Inventor: Tim M. Watkins, Chesterfield, MO (US)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/528,460

(22) Filed: Dec. 4, 2023

(65) Prior Publication Data

US 2024/0111900 A1    Apr. 4, 2024

Related U.S. Application Data

(63) Continuation of application No. 17/897,891, filed on Aug. 29, 2022, now Pat. No. 11,835,996, which is a
(Continued)

(51) Int. Cl.
*G06F 21/62* (2013.01)
*G06F 21/36* (2013.01)
(Continued)

(52) U.S. Cl.
CPC .......... *G06F 21/6254* (2013.01); *G06F 21/36* (2013.01); *G16H 10/60* (2018.01); *H04L 9/3213* (2013.01)

(58) Field of Classification Search
CPC ..... G06F 21/6254; G06F 21/36; G16H 10/60; H04L 9/3213
See application file for complete search history.

(56) References Cited

U.S. PATENT DOCUMENTS

| 9,430,652 B1 | 8/2016 | Mattsson et al. |
| 9,684,800 B2 | 6/2017 | Mattsson et al. |
(Continued)

FOREIGN PATENT DOCUMENTS

| CN | 103327002 A | 9/2013 |
| DE | 102018103278 A1 | 8/2019 |

OTHER PUBLICATIONS

Mitu Kumar Debnath et al., "A secure revocable personal health record system with policy-based fine-grained access control", 2015 13th Annual Conference on Privacy, Security and Trust (PST), Sep. 3, 2015, 9 pages.
(Continued)

*Primary Examiner* — Izunna Okeke
(74) *Attorney, Agent, or Firm* — Armstrong Teasdale LLP

(57) ABSTRACT

Described herein is a data security system for enabling tokenized access to sensitive data, including a token provider configured to initiate a secure connection with a remote client computing device of a first data subject, and receive, from the remote client computing device, a request for an access token to provide a service provider with access to sensitive data associated with the first data subject. The request includes a data definition and authorization parameters including a data source identifier. The token provider is also configured to generate the access token that enables access to the sensitive data from the data source, store the access token in a token database, and transmit, to the remote client computing device, a response including the access token and instructions that enable the remote computing device to display the access token to the first data subject or transmit the access token to the service provider.

20 Claims, 12 Drawing Sheets

Related U.S. Application Data continuation of application No. 16/936,158, filed on Jul. 22, 2020, now Pat. No. 11,429,749.

(51) Int. Cl.
*G16H 10/60* (2018.01)
*H04L 9/32* (2006.01)
*H04L 29/06* (2006.01)

(56) References Cited

U.S. PATENT DOCUMENTS

| | | |
|---|---|---|
| 9,953,171 B2 | 4/2018 | Saxena et al. |
| 10,489,784 B2 | 11/2019 | Bailey et al. |
| 10,558,963 B2 | 2/2020 | Desai et al. |
| 10,635,828 B2 | 4/2020 | Lin |
| 11,004,548 B1 | 5/2021 | Austin et al. |
| 2003/0196087 A1 | 10/2003 | Stringer et al. |
| 2012/0331529 A1 | 12/2012 | Ibel et al. |
| 2016/0080364 A1 | 3/2016 | Karimzadeh et al. |
| 2017/0048221 A1* | 2/2017 | Melton ............... G06F 21/6245 |
| 2017/0053139 A1 | 2/2017 | Schenk et al. |
| 2017/0076109 A1 | 3/2017 | Kaditz et al. |
| 2017/0076281 A1 | 3/2017 | Dawkins et al. |
| 2017/0344704 A1 | 11/2017 | Chu |
| 2018/0032757 A1 | 2/2018 | Michael |
| 2018/0089451 A1 | 3/2018 | Lin |
| 2018/0114036 A1 | 4/2018 | Spodak et al. |
| 2019/0109830 A1 | 4/2019 | McFarland et al. |
| 2019/0295700 A1 | 9/2019 | Weinstock et al. |
| 2019/0304574 A1 | 10/2019 | Weinstock et al. |
| 2020/0145820 A1 | 5/2020 | Hoyer |
| 2020/0202996 A1 | 6/2020 | Rastogi |
| 2020/0273017 A1 | 8/2020 | Mossoba et al. |
| 2020/0286607 A1 | 9/2020 | Abuzeni |
| 2020/0311299 A1 | 10/2020 | Amar |
| 2020/0327540 A1 | 10/2020 | Chavarria et al. |
| 2021/0058404 A1 | 2/2021 | D'Agostino |
| 2021/0089667 A1 | 3/2021 | Kadiyala et al. |
| 2021/0281409 A1 | 9/2021 | Apsingekar et al. |
| 2021/0295280 A1 | 9/2021 | Blakesley et al. |

OTHER PUBLICATIONS

PCT International Search Report and Written Opinion, Application No. PCT/US2021/034496, dated Sep. 06, 2021, 10 pps.

PCT International Search Report and Written Opinion, Application No. PCT/US2021/034508, dated Sep. 6, 2021, 10 pps.

Roderick L B Neame, "Privacy protection for personal health information and shared care records", Informatics in Primary Care, vol. 21, No. 2, Feb. 2014, pp. 84-91.

Wang et al., "Secure Cloud-Based EHR System Using Attribute-Based Cryptosystem and Blockchain", J. Med. Syst. 42, 152 (2018).

Wu et al., "Efficient and privacy-preserving tracable attribute-based encryption in blockchain", Ann. Telecommun. 74, 401-411 (2019).

European Extended Search Report, Application No. 21846827.0, dated Mar. 1, 2024, 9 pps.

* cited by examiner

SYSTEMS AND METHODS FOR TOKENIZATION OF PERSONALLY IDENTIFIABLE INFORMATION (PII) AND PERSONAL HEALTH INFORMATION (PHI)

CROSS-REFERENCE TO RELATED APPLICATIONS

This application is a continuation application of and claims priority to U.S. patent application Ser. No. 17/897,891, filed Aug. 29, 2022, which is a continuation application of and claims priority to U.S. patent application Ser. No. 16/936,158, filed Jul. 22, 2020, which is now U.S. Pat. No. 11,429,749, the entire contents and disclosures of which are hereby incorporated herein by reference in their entirety.

BACKGROUND

This disclosure relates generally to the field of data security and, more specifically, to the tokenization of personally identifiable information (PII) and personal health information (PHI).

There exist many situations in which individuals need to provide sensitive data, such as PII and/or PHI, to service providers, such as customer service representatives, bankers, health care providers, insurance claim adjusters, and the like. However, providing this sensitive data can be tedious and redundant. Moreover, many individuals may be uncomfortable providing their sensitive data, depending on the environment. For example, an individual in a public setting may not feel comfortable providing a credit card number or Social Security number to a service provider over the phone.

Therefore, there is a need for a system that minimizes redundancies in sharing sensitive data with trusted service providers and that maintains the security of the sensitive data.

BRIEF DESCRIPTION

In one aspect, a data security system for enabling tokenized access to sensitive data includes a token provisioning computing device including a processor communicatively coupled to a memory device. The processor is programmed to generate an access token that is associated with and enables access to defined sensitive data associated with a first data subject from one or more data sources according to one or more authorization parameters, and store the access token in a token database with the one or more authorization parameters, the one or more authorization parameters including a data source identifier indicating where the defined sensitive data is stored. The processor is further programmed to transmit the access token to a remote client computing device of the first data subject, and receive, from a service provider computing device separate from the remote client computing device, a data access request including an inputted access token. The processor is also programmed to compare the inputted access token to the access token stored in the token database, and, when the inputted access token matches the stored access token, transmit, to the service provider computing device, the defined sensitive data being requested and associated with the stored access token.

In another aspect, a computer-implemented method for enabling tokenized access to sensitive data is implemented using a data security system including a token provisioning computing device including a processor communicatively coupled to a memory device. The method includes generating an access token that is associated with and enables access to defined sensitive data associated with a first data subject from one or more data sources according to one or more authorization parameters, storing the access token in a token database with the one or more authorization parameters, the one or more authorization parameters including a data source identifier indicating where the defined sensitive data is stored, transmitting, to the remote client computing device of the first data subject, a response including the access token, and receiving, from a service provider computing device separate from the remote client computing device, a data access request including an inputted access token. The method also includes comparing the inputted access token to the access token stored in the token database, and when the inputted access token matches the stored access token, transmitting, to the service provider computing device, the defined sensitive data being requested and associated with the stored access token.

In a further aspect, a non-transitory computer-readable storage medium having computer-executable instructions stored thereon is provided. When executed by a processor of a token provisioning computing device of a data security computing system, the computer-executable instructions cause the processor to generate an access token that is associated with and enables access to defined sensitive data associated with a first data subject from one or more data sources according to one or more authorization parameters, store the access token in a token database with the one or more authorization parameters, the one or more authorization parameters including a data source identifier indicating where the defined sensitive data is stored, and transmit the access token to a remote client computing device of the first data subject. The instructions also cause the processor to receive, from a service provider computing device separate from the remote client computing device, a data access request including an inputted access token, compare the inputted access token to the access token stored in the token database, and, when the inputted access token matches the stored access token, transmit, to the service provider computing device, the defined sensitive data being requested and associated with the stored access token.

In one aspect, a data security system for enabling tokenized access to sensitive data is provided. The data security system includes a token provisioning computing device including a processor communicatively coupled to a memory device. The token provisioning computing device is configured to initiate a secure connection with a remote client computing device of a first data subject, and receive, from the remote client computing device of the first data subject, a request for an access token to provide a service provider computing device with access to sensitive data associated with the first data subject. The request includes a data definition of the sensitive data to which access is to be provided and one or more authorization parameters including one or more data source identifiers of a respective one or more data sources at which the defined sensitive data is stored. The token provisioning computing device is also configured to generate the access token that enables access to the defined sensitive data from the one or more data sources according to the one or more authorization parameters, store the access token in a token database with the data definition and the one or more authorization parameters, and transmit, to the remote client computing device of the first data subject, a response including the access token and instructions that enable the remote computing device to at least one of display the access token to the first data subject and transmit the access token to the service provider computing device.

In another aspect, a computer-implemented method for enabling tokenized access to sensitive data is provided. The method is implemented using a data security system including a token provisioning computing device including a processor communicatively coupled to a memory device. The method includes initiating, by the token provisioning computing device, a secure connection with a remote client computing device of a first data subject, and receiving, by the token provisioning computing device from the remote client computing device of the first data subject, a request for an access token to provide a service provider computing device with access to sensitive data associated with the first data subject. The request includes a data definition of the sensitive data to which access is to be provided and one or more authorization parameters including one or more data source identifiers of a respective one or more data sources at which the defined sensitive data is stored. The method also includes generating, by the token provisioning computing device, the access token that enables access to the defined sensitive data from the one or more data sources according to the one or more authorization parameters, storing, by the token provisioning computing device, the access token in a token database with the data definition and the one or more authorization parameters, and transmitting, by the token provisioning computing device to the remote client computing device of the first data subject, a response including the access token and instructions that enable the remote computing device to at least one of display the access token to the first data subject and transmit the access token to the service provider computing device.

In a further aspect, a non-transitory computer-readable storage medium having computer-executable instructions stored thereon is provided. When executed by a processor of a token provisioning computing device of a data security computing system, the computer-executable instructions cause the processor to initiate a secure connection with a remote client computing device of a first data subject, and receive, from the remote client computing device of the first data subject, a request for an access token to provide a service provider computing device with access to sensitive data associated with the first data subject. The request includes a data definition of the sensitive data to which access is to be provided and one or more authorization parameters including one or more data source identifiers of a respective one or more data sources at which the defined sensitive data is stored. The computer-executable instructions also cause the processor to generate the access token that enables access to the defined sensitive data from the one or more data sources according to the one or more authorization parameters, store the access token in a token database with the data definition and the one or more authorization parameters, and transmit, to the remote client computing device of the first data subject, a response including the access token and instructions that enable the remote computing device to at least one of display the access token to the first data subject and transmit the access token to the service provider computing device.

BRIEF DESCRIPTION OF THE DRAWINGS

FIG. 1 is a schematic diagram illustrating a first example data security system for enabling tokenized access to sensitive data, in accordance with the present disclosure.

FIG. 2 is a schematic diagram illustrating a second example data security system for enabling tokenized access to sensitive data including personal health data from one or more data sources, in accordance with the present disclosure.

FIG. 3 illustrates an example user interface displayed on a client computing device of the data security computing system shown in FIG. 1, including generation of a data definition.

FIGS. 4-9 are swim lane diagrams illustrating implementation of a tokenized data access method using components of the data security computing systems shown in FIGS. 1 and 2.

FIG. 10 illustrates an example client computing device that may be used with the data security computing systems shown in FIGS. 1 and 2.

FIG. 11 illustrates an example server computing device that may be used with the data security computing systems shown in FIGS. 1 and 2.

FIG. 12 illustrates an example tokenized data access method that may be implemented using the data security computing systems shown in FIGS. 1 and 2.

Like numbers in the Figures indicate the same or functionally similar components.

DETAILED DESCRIPTION

Figure 1:
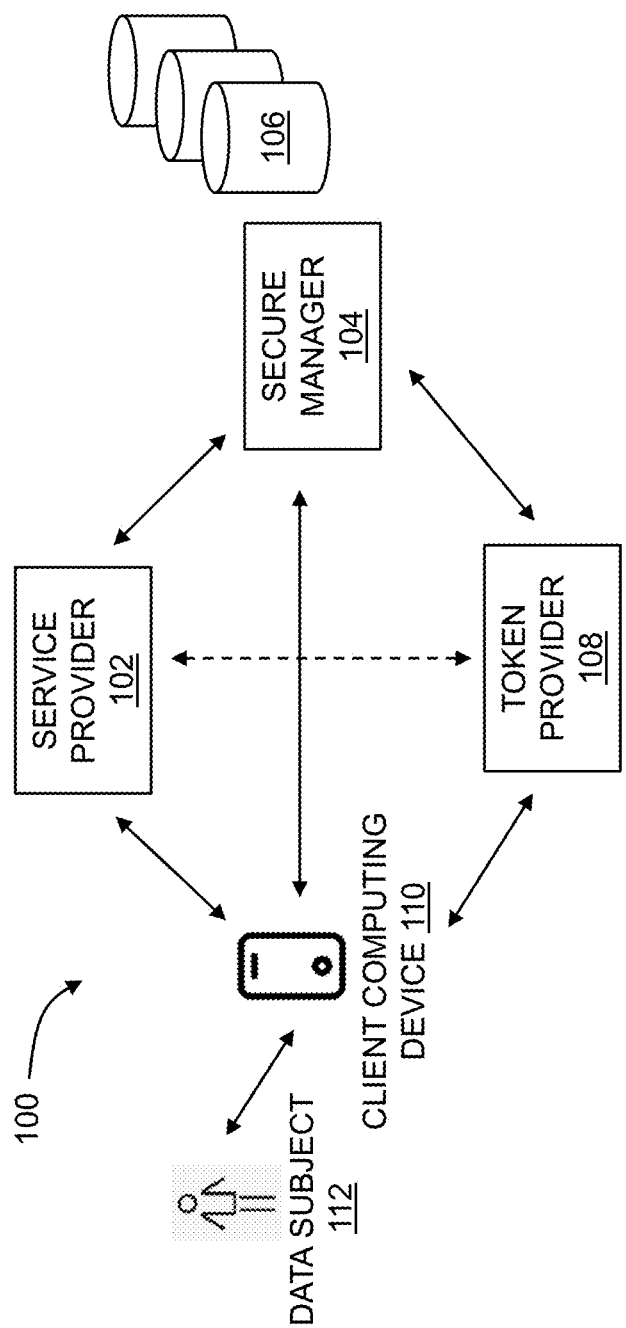
FIGS. 1-12 show example embodiments of the methods and systems described herein.

The present disclosure relates to a data security computing system that enables tokenized access to sensitive data, such as personally identifiable information (PII) and/or personal health information (PHI). In particular, rather than providing data directly to a service provider, an individual (also referred to herein as a "data subject" or "token requestor"), who is also a subject and/or an originating source of the PII and/or PHI, may request a token, to be securely provided to the service provider, that enables the service provider to securely access stored PII and/or PHI data associated with that individual or data subject. This process eliminates redundancies while enhancing data security as well as data accuracy. Specifically, the individual need not repetitively provide the same data elements to many different services, which is tedious and time-consuming but also vulnerable to user error (either by the individual or the service provider). The service provider uses the token to access data that is both securely stored and accurately transmitted (and, in some embodiments, accurately locally entered at the service provider).

In the example embodiment, a data subject (e.g., an individual) registers with the data security computing system and provides their PII for secure storage. The data subject provides their PII as one or more data elements, for example, using a client computing device. The client computing device is communicatively coupled to a centralized server computing device referred to herein as a "secure manager." The secure manager is configured to store PII in one or more centralized or decentralized databases. The secure manager stores the PII in encrypted or otherwise secured format within the database(s). As described further herein, the secure manager is configured to limit access to the data stored within the databases, specifically, to access defined by an access token requested and provided by the data subject to a service provider.

In one embodiment, the client computing device is communicatively coupled to the secure manager via a secure communication channel that is initiated in a web browser or software application ("app") environment. For example, the client computing device stores and executes an app that initiates a secure communication channel with the secure manager. The app may cause display of one or more screens on the client computing device, including data entry and/or data provision screens. To provide their PII for storage, the data subject may manually enter data elements into their client computing device, such as via a manually fillable form. Alternatively, the client computing device may automatically populate certain fields or data elements using stored information (e.g., name, date of birth, address, etc.). The data subject controls which data elements to provide for storage to the secure manager, and may choose to populate fewer than all available fields. The data subject transmits the PII as one or more data elements to the secure manager for secure storage in one or more database(s). In some embodiments, PII associated with the data subject is provided to the secure manager by other data sources (e.g., insurance companies may provide claim details/history, banks may provide loan information, etc.). The secure manager may additionally or alternatively store a pointer to PII that is stored in other locations (e.g., other than the database of the secure managers).

The secure manager indexes the stored PII according to one or more variables, such as a subject identifier, or any other variable that uniquely identifies the data subject. The subject identifier may be provided by the data subject (e.g., as a phone number or SSN), or may be automatically generated by the secure manager during the registration phase (e.g., as a pseudo-random alphanumeric code). In such cases, the secure manager returns the subject identifier to the client computing device for storage (e.g., within the secure app environment). The client computing device may include the subject identifier in further communications with service providers and/or the secure manager, such that the data subject's PII is easily retrieved using the subject identifier. The data subject may use their client computing device to add, delete, and/or modify their stored PII at any time.

In some embodiments, the data subject wishes to store and retrieve—via access token— PHI, in accordance with the present disclosure. In some cases, the data subject provides PHI in the same manner described above with respect to PHI. Additionally or alternatively, at least one data element of PHI is stored in specific secure database(s) managed by health care providers (HCP) or HCP networks/systems (collectively referred to herein as "HCP data managers"). For example, a data subject typically does not have access to their full medical record for personal storage thereof. Rather, the HCP data managers include medical systems, hospital systems, individual HCPs, and the like, and are specifically configured for management, storage, and provision of PHI. It is recognized that in some jurisdictions, such as the United States, PHI, such as medical records, is stored in disparate formats among various HCP data managers. Accordingly, in such jurisdictions, there exist one or more record integrators (e.g., EPIC, CERNER, ALLSCRIPTS, etc., which are all registered trademarks of their respective owners). These record integrators manage integration and unification of PHI, such as medical records, between a plurality of HCP data managers, such that all HCP service providers associated with a record integrator can access a unified, centralized record for a data subject. The record integrator may store PHI and/or may provide an interface to access PHI stored at disparate HCP data mangers.

It is further realized that stored PHI, such as medical records, may be currently stored in unified formats in other jurisdictions, and/or a true universal medical record (UMR) applicable to all jurisdictions may eventually be created and used. In such cases, the record integrator described herein may not be required, and direct contact with HCP data managers may be implemented without departing from the scope of the disclosure.

A data subject may provide their PHI as one or more data elements for storage by the secure manager and/or may select which data elements of their PHI is available for access (e.g., by one or more service providers such as HCPs) from one or more HCP data managers via an access token. The data subject may use their client computing device to communicate with the secure manager and/or one or more HCP data managers using a web browser and/or app environment. The data subject may need to communicate with a plurality of HCP data managers, for example, where the data subject has HCPs in different medical/healthcare systems. Alternatively, the data subject uses their client computing device to communicate with one or more record integrators using the web browser and/or app environment, for example, to identify HCP data managers at which their PHI is stored.

In any of the above cases, the client computing device is communicatively coupled to the "PHI receiving device" (e.g., the secure manager, the HCP data manager(s), and/or the record integrator(s)) via a secure communication channel that is initiated in the web browser or app environment. For example, the client computing device stores and executes an app that initiates a secure communication channel with the PHI receiving device. The app may cause display of one or more screens on the client computing device, including data entry and/or data provision screens. To provide their PHI for storage, the data subject may manually enter data elements into their client computing device, such as via a manually fillable form. The data subject controls which data elements to provide for storage to the PHI receiving device, and transmits the PHI as one or more data elements to the PHI receiving device for secure storage in one or more database (s). Alternatively, the PHI receiving device may cause display of any/all data elements of PHI that are already stored at and/or accessible to the PHI receiving device, such as medical records, surgical histories, medication/prescription records, and the like. The PHI receiving device may store the PHI and/or may store a pointer to a location at which the PHI is stored (e.g., a secure manager may store a pointer to a location at an HCP data manager). The data subject controls which stored data element(s) of PHI to make available for later access via an access token.

The PHI receiving device indexes the stored PHI according to one or more variables, such as a subject identifier, or any other variable that uniquely identifies the data subject. The subject identifier may be provided by the data subject (e.g., as a phone number or SSN), may be pre-existing (e.g., a UMR identifier or electronic medical record (EMR) identifier), or may be automatically generated by the PHI receiving device during the registration phase (e.g., as a pseudo-random alphanumeric code). In such cases, the PHI receiving device returns the subject identifier to the client computing device for storage (e.g., within the secure app environment). The client computing device may include the subject identifier in further communications with service providers, HCP data manager(s), and/or record integrator(s), such that the data subject's PHI is easily retrieved using the subject identifier. The data subject may use their client computing device to add, delete, and/or modify their stored PHI at any time.

The data subject (e.g., an individual) may wish to provide access to their stored PII and/or PHI at a later date, to a service provider. A service provider may include, for example, an insurance claims manager, a customer service representative, a health care provider, and the like. The service provider requests various data elements of PII and/or PHI from the data subject. For example, the service provider may ask the data subject to verbally provide PII and/or PHI, to physically write down their PII and/or PHI on one or more forms, or to provide PII and/or PHI in electronic format (e.g., in an electronic form). The data subject may not wish to provide that PII and/or PHI for one or more reasons. For example, the data subject may be in a public place where verbalizing their PII and/or PHI may make the PII and/or PHI vulnerable to being overheard. Additionally or alternatively, the data subject may merely not wish to provide their data in such a tedious and redundant fashion.

Accordingly, to maintain security of their PII and/or PHI and/or to avoid physically or manually providing this data, the data subject requests an access token, which the service provider can use to securely access at least a portion of the data subject's stored PII and/or PHI. In the example embodiment, the data subject uses their client computing device to request such an access token. The data subject initiates a secure communication channel with a token provider within a web browser and/or app environment. The token provider is configured to generate tokens that enable data subject-defined access to the data subject's PII and/or PHI. In some embodiments, the token provider is the same entity or is otherwise associated with the secure manager, record integrator, and/or HCP data manager (collectively "data storage providers"). That is, one (business) entity many provide data storage services as well as token provisioning services. Notably, in such embodiments, the token provider is an independent computing device or is an independent processing module of the same computing device, such that the token provision services remain independent of the data storage services. In other embodiments, the token provider is wholly independent of any data storage providers.

To request the access token, the data subject (e.g., the individual) selects which data elements of PII and/or PHI to allow the service provider access to. The client computing device displays a list of all available PII and/or PHI. The list may be dynamically populated by one or more data storage providers. For example, the app environment may enable an API connection between the data storage providers, such that the real-time currently available PII and/or PHI is shown in the list. Alternatively, the list may be populated by the client computing device based upon data that is periodically (e.g., daily, weekly, monthly) provided by the data storage providers, reflecting the data elements available as of the last periodic update.

The data subject selects one or more data elements of PII and/or PHI to allow the service provider access (e.g., using checkboxes, radio buttons, a drag-and-drop interface, etc.). The selected data may be referred to herein as a "data definition," which defines which data elements the service provider will be allowed access to. The data subject may also select one or more authorization parameters that further define how the service provider is allowed to access the data subject's PII and/or PHI. The authorization parameters may include an authorization date or validity date parameter. This parameter defines how long the service provider is allowed access to and/or local storage of the data subject's PII and/or PHI. For example, where a data subject is providing PII and/or PHI to an insurance claim adjuster, the data subject may authorize the insurance adjuster to access their PII and/or PHI for a period corresponding to the claim processing timeline, such as three months or six months. As another example, where the data subject is providing PII (e.g., an SSN) to a customer service provider (e.g., for authentication to a bank), the data subject may only authorize access for five or ten minutes.

The authorization parameters may include one or more authorized service providers. For example, where a data subject wishes to allow data access to one HCP (e.g., one specialist's office) in a network of HCPs, the data subject many only authorize access to PHI for that one HCP, but not the network; or to only a select number of HCPs (e.g., the specialist and an associated physical therapist) within the network. As another example, where a data subject is having their vehicle serviced as a result of an automobile accident, in accordance with an insurance claim, the data subject may only authorize one specific service provider location (e.g., repair shop) in a nationwide network of such service providers.

The authorization parameters may include a data access source. In particular, to allow access to PII and/or PHI, the data subject may select a data source to identify, to the service provider, secure manager, or record integrator, where the service provider, secure manager, or record integrator is able to access the data subject's data. In some cases, the data subject may authorize access—for an HCP within a healthcare network—to data from an HCP data manager associated with that same healthcare network, but not to data from another, unrelated healthcare provider or network. In some embodiments of the present disclosure, the data subject may be required to select a data source—e.g., an HCP data manager—from which data can be accessed, such as where the data sources may include variations of PHI or PHI formatted in a way that is incongruous with a system of the service provider.

The authorization parameters may include additional or alternative parameters, such as a date range of accessible data. For example, a data subject may authorize access to PII and/or PHI within a date range of the last five or ten years, but not any PII and/or PHI from dates outside of that range.

The data subject, after making all necessary and/or desired selections, requests an access token. The client computing device transmits an access token request to the token provider. The request includes the data definition and any associated authorization parameters. In some embodiments, the request also includes the subject identifier (e.g., a phone number, SSN, UMR/EMR identifier, other unique identifier). The request may include still other data elements, such as authentication data elements that may be used to authenticate the request and/or the data subject. For example, the data subject may be required to enter log-in and/or authentication credentials to open their app and/or initiate the secure connection with the token provider. In such cases, the client computing device may transmit an indicator, in the token request message, that indicates the data subject successfully logged-in and/or authenticated themselves to the app prior to generating the token request.

The token provider receives the request from the client computing device and processes the request to generate an access token. The token provider transmits the access token back to the client computing device, such that the data subject may provide the access token to the service provider. The access token is associated with and/or includes the data definition and authorization parameters, and is specific to this particular instance in which the data subject desires to give this particular service provider access to the selected PII and/or PHI. That is, in the example embodiment, the access token is not usable in any other instance. In an alternative embodiment, the access token may be authorized for use by that particular service provider in multiple instances, to access the same selected PII and/or PHI—however, such repeated access may require specific authorization by the data subject (e.g., via an authorization parameter that enables repeat usage of the access token, or by requesting confirmation from the data subject if/when a service provider attempts to re-use an access token).

In the example embodiment, the access token is embodied as an alphanumeric code, and the data subject provides the access token to the service provider verbally, shows the access token to the service provider on their client computing device, or provides the access token electronically to the service provider (e.g., by typing or pasting the code into a fillable field). In some alternative embodiments, the access token may be otherwise embodied, such as a string or message transmittable over near-field communication (NFC, e.g., by "tapping" the client computing device at a receiver of the service provider), or as image content (e.g., a bar code or QR code that may be scanned by the service provider). In some embodiments, the client computing device also provides the subject identifier to the service provider.

In some embodiments, the token provider authenticates the data subject before generating and/or providing the requested access token. In some such embodiments, the token provider uses authentication elements provided in the token request to authenticate the data subject. In some embodiments, the token provider transmits an authentication request message back to the client computing device, which includes instructions that cause the client computing device to prompt the data subject to provide authentication credentials (e.g., a biometric identifier, a password, a PIN, answer(s) to security question(s), etc.). In these embodiments, the token provider receives an authentication response message back from the client computing device including the data subject's responses, and processes those responses (e.g., by comparing the data subject's input to stored authentication credentials) to authenticate the data subject.

It is contemplated that, in some embodiments, the service provider may request an access token from the token provider, on behalf of the data subject. In such embodiments, the token provider, upon receiving a token request message from the service provider, will request confirmation, a data definition, and/or authorization parameters from the data subject (e.g., by transmitting a confirmation request message to the client computing device associated with the data subject). When the data subject confirms the request, and provides any associated data definition and/or authorization parameters, the token provider generates the access token, as described above, and transmits the access token directly to the service provider (e.g., in a token response message).

The token provider stores the access token in a database. The token provider may also store the data definition and/or the authorization parameters along with the access token. The token provider allows the data subject to access any generated access token(s) via their client computing device. The data subject may review which access tokens have been generated, which service provider(s) have access to which data element(s), how long authorization was granted, and the like. In some embodiment, the data subject is able to select an access token for modification or revocation. The data subject may add or remove data element(s) they wish to provide access to, and/or may modify the authorization parameters (e.g., increase or decrease the period of data validity). The data subject may revoke any access token. In response to the data subject modifying or revoking an access token, the token provider may be configured to generate a message indicating the modification/revocation, for transmission to the associated service provider (either directly, from the token provider, or indirectly, via the client computing device). In response to the data subject revoking an access token, the token provider may delete the stored access token and/or disable the access token, which prevents further access to the data subject's data by the service provider. Additionally, where an access token has an associated authorization parameter that specifies a validity date, when the validity date is reached (or passes), the token provider may delete the stored access token and/or disable the access token, which prevents further access to the data subject's data by the service provider.

The service provider receives the access token from the data subject, as described above. The service provider provides the access token to an interface executed on a service provider computing device, where the interface is maintained by the data storage provider in one example embodiment. The service provider may be a human that enters the access token, for example, via a keyboard, mouse, and the like. The service provider may additionally or alternatively include an input device, such as an NFC receiver, scanner, or computing device that receives the access token electronically. The data storage provider (e.g., secure manager, HCP data manager, record integrator) receives the access token from the service provider computing device.

The data storage provider initiates a secure communication channel with the token provider. Where the data storage provider and token provider are a same entity, the secure communication channel may include communicative coupling between independent computing devices or processing modules. Where the data storage provider and token provider are not a same entity, the secure communication channel may be any secure communication channel between remote computing devices.

As described in greater detail herein, the data storage provider exchanges messages with the token provider to validate the access token received from the service provider. The data storage provider sends a validation request message to the token provider, the validation request message including the access token and, in some embodiments, a subject identifier. The subject identifier may be the same as the subject provider transmitted from the client computing device, or may be a separate subject identifier. The token provider compares the received access token (and, in some embodiments, the subject identifier) to the stored access token to determine whether the received access token is valid. When the access token is invalid, the token provider returns a validation response including an access denial, and an indication that the access token is invalid. When the access token is valid, the token provider returns a validation response including an access approval. In some embodiments, the access approval may include the data definition and/or the authorization parameters associated with the valid stored access token. In some embodiments, the access token itself defines what data is accessible.

When the data storage provider receives the validation response including the access approval (and, in some embodiments, the data definition and/or authorization parameters), the data storage provider provides access to PII and/or PHI under the conditions of the access token. That is, the data storage provider transmits the approved and authorized data back to the service provider computing device. Therefore, the service provider computing device receives (and may locally store) the PII and/or PHI without the data subject having to provide the PII and/or PHI, especially where the conditions of such provision may make the PII and/or PHI vulnerable to unauthorized access.

As used herein, personally identifiable information (PII) refers to information that, when used alone or in combination, can identify a specific individual. PII may include direct identifiers (e.g., name, Social Security Number (SSN), phone number, etc.) or indirect identifiers, also known as quasi-identifiers, that can be combined together to identify the individual (e.g., date of birth, address, etc.). PII may include, but is not limited to, name, address, phone number, SSN, date of birth, educational history, social media identifiers, IP address or other device/network identifiers, driver's license number, passport number, payment account/device (e.g., credit card) information, other financial information, and the like.

Personal health information (PHI) is information related to an individual's health or health history and that is protected by various data protection laws and regulations (e.g., HIPAA protections, in the United States). Therefore, HCP data managers, as described herein, may be computing systems that are specifically secured and managed in accordance with those data protection laws and regulations. PHI may include some elements of PII (e.g., date of birth) but is generally considered a more specific set of details that center on an individual's personal and private health data. PHI includes, but is not limited to, name, date of birth, medical records (including Universal Medical Records (UMR) and/or Electronic Medical Records (EMR) and identifiers thereof), height, weight, health insurance information, medical history, surgical history, family medical history, medications, allergies, and the like.

Although PII and PHI are referred to separately herein, it should be understood that the systems and methods described herein may be individually, collectively, and/or equally applicable to PII and PHI. More specifically, PHI may be limited to more specific and specialized data sources, but the methods for tokenized access and retrieval of PII may be generally applicable to PHI as well.

The data security system described herein improves over conventional methods of providing sensitive data, including PII and/or PHI, to service providers. Specifically, the data is secured and not vulnerable to unauthorized access (e.g., by overhearing, by written or printed details being misplaced or copied, etc.). This data security system reduces data subject input requirements to a few selections and commands, and centralizes storage and retrieval to secured computing devices and databases. Moreover, this data security system improves data accuracy across multiple devices by ensuring a singular and/or unified data source is providing PII and/or PHI to all requesting service providers.

The technical problems addressed by this system include at least one of: (i) vulnerability of PII and/or PHI to unauthorized access when transmitted verbally or on paper to service providers; (ii) lack of centralized PII and/or PHI data sources and access points; (iii) discrepancies in data between service providers due to user entry error and/or varied system formats/interfaces; and (iv) time-consuming, inefficient, and redundant provision of PII and/or PHI to various service providers (e.g., manual and/or verbal entry).

The methods and systems described herein may be implemented using computer programming or engineering techniques including computer software, firmware, hardware, or any combination or subset thereof, wherein the technical effects may be achieved by: (a) initiating a secure connection with a remote client computing device of a first data subject; (b) receiving, from the remote client computing device of the first data subject, a request for an access token to provide a service provider computing device with access to sensitive data associated with the first data subject, wherein the request includes a data definition of the sensitive data to which access is to be provided and one or more authorization parameters including one or more data source identifiers of a respective one or more data sources at which the defined sensitive data is stored; (c) generating the access token that enables access to the defined sensitive data from the one or more data sources according to the one or more authorization parameters; (d) storing the access token in a token database with the data definition and the one or more authorization parameters; and/or (e) transmitting, to the remote client computing device of the first data subject, a response including the access token and instructions that enable the remote computing device to at least one of display the access token to the first data subject and transmit the access token to the service provider computing device.

The resulting technical benefits achieved by this system include at least one of: (i) providing a secure, centralized access point for PII and/or PHI; (ii) unification and standardization of PII and/or PHI provided to multiple service providers across disparate systems; and (iii) securing the transmission of PII and/or PHI between data subjects and service providers while reducing user effort and time required.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one embodiment, a computer program is provided, and the program is embodied on a computer readable storage medium. In an example embodiment, the system is executed on a single computer system, without requiring a connection to a server computer. In a further embodiment, the system is being run in a Windows® environment (Windows is a registered trademark of Microsoft Corporation, Redmond, Washington). In yet another embodiment, the system is run on a mainframe environment and a UNIX® server environment (UNIX is a registered trademark of X/Open Company Limited located in Reading, Berkshire, United Kingdom). The application is flexible and designed to run in various different environments without compromising any major functionality. In some embodiments, the system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes.

As used herein, an element or step recited in the singular and proceeded with the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

FIG. 1 includes a schematic diagram illustrating an example embodiment of a data security computing system 100 for enabling tokenized access to sensitive data, in accordance with the present disclosure. In the illustrated embodiment, data security computing system 100 includes a plurality of service providers 102, at least one secure manager 104 communicatively coupled to one or more secure databases 106 for securing storing sensitive data (including PII and/or PHI), and at least one token provisioning computing device ("token provider") 108. Service providers 102 collectively include service provider computing devices (e.g., desktop computing devices, laptop computing devices, tablets, etc.) and human operators that may employ service provider computing devices (e.g., to enter data). Service providers 102 are communicatively coupled to secure managers 104 to transmit access tokens thereto and to request and receive sensitive data therefrom. In addition, secure managers 104 are communicatively coupled to token provider 108, to validate received access tokens before providing sensitive data to service providers 102. In some embodiments, service providers 102 are communicatively coupled to token provider 108, and may request/receive access tokens directly therefrom.

In addition, client computing devices 110, operated by individuals or data subjects 112, are communicatively coupled to token provider 108. Data subject 112 operates client computing device 110 to request access tokens from token provider 108 over a secure communication channel. Data subject 112 operates client computing device 110 to select data elements to provide access to, as well as authorization parameters of that access, as described herein. Data subject 112 also uses client computing device 110 to receive access tokens for provision to service provider 102 (via data subject 112, such as verbally or in written form, or directly, such as via NFC communication). Client computing devices 110 are also communicatively coupled to secure manager 104, such that data subject 112 may provide PII and/or PHI for storage, by secure manager 104, within database(s) 106.

Secure manager 104 may include any suitable computing device(s), such as one or more server computing device(s), cloud-based computing and/or storage systems, and/or any other device(s). Secure manager 104 stores sensitive data in databases 106, which are any suitable secure storage devices, including any suitable encryption and/or access restriction mechanisms.

Likewise, token provider 108 may include any suitable computing device(s), such as one or more server computing device(s), databases, cloud-based computing and/or storage systems, and/or any other device(s), token databases/vaults, and/or encryption mechanisms. As described above, token provider 108 may be a part of and/or associated with secure manager 104. Alternatively, token provider 108 is independent from secure manager 104.

Client computing device 110 may include any device capable of accessing the Internet and communicating with service provider 102, secure manager 104, and/or token provider 108, including a laptop computing device, mobile phone (e.g., smartphone), tablet, desktop computing device, and the like. Moreover, data subject 112 may operate more than one client computing device 110 to perform the processes described herein. For example, data subject 112 may operate a desktop client computing device 110 to provide PII and/or PHI for storage by secure manager 104, and may operate a smartphone client computing device 110 to request an access token from token provider 108, receive the access token from token provider, and/or provide the access token to service provider 102.

Figure 2:
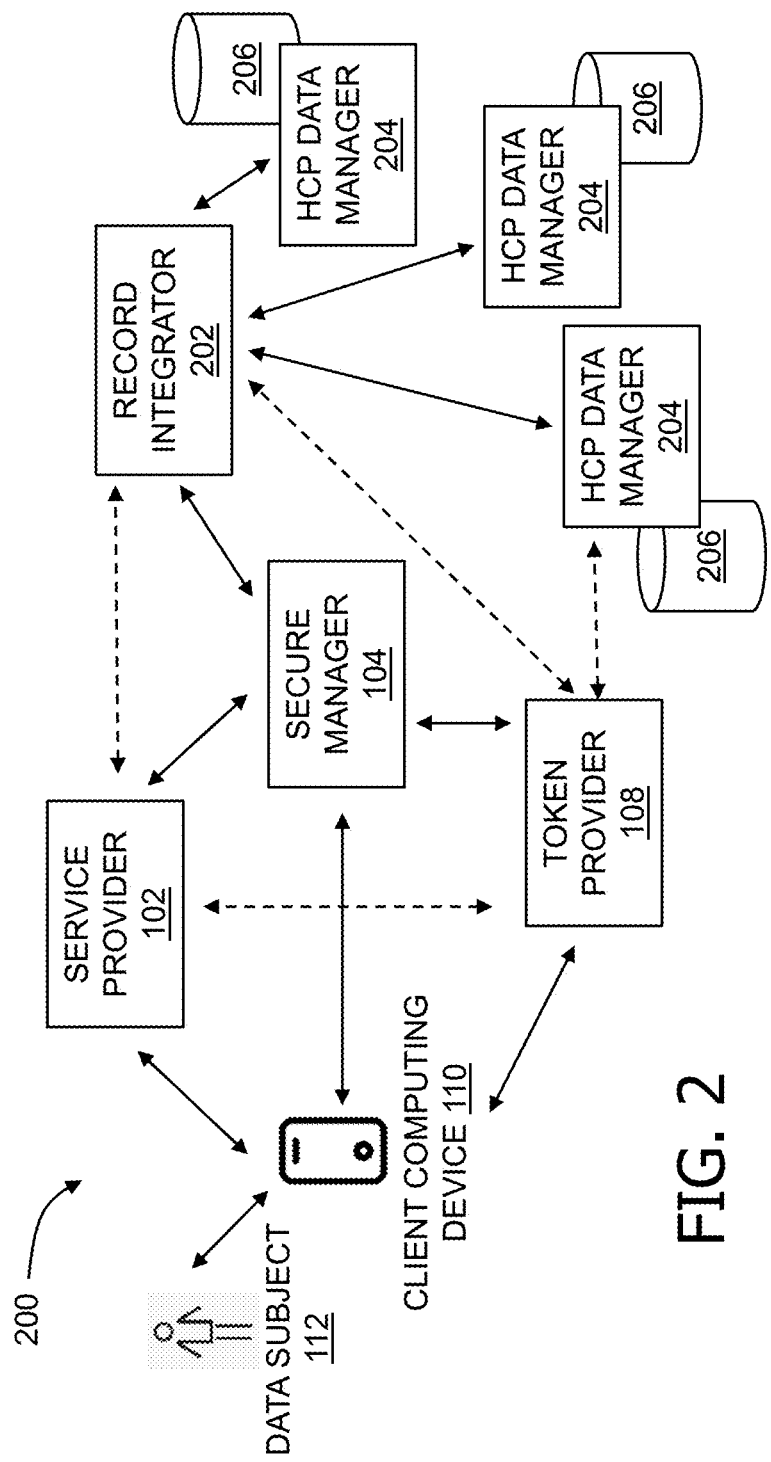

FIG. 2 illustrates another example embodiment of a data security computing system 200 in accordance with the present disclosure. Like numerals are used to refer to like elements of data security computing system 100 depicted in FIG. 1 and data security computing system 200 depicted in FIG. 2. Specifically, data security computing system 200 also includes at least one service provider 102, a secure manager 104, at least one token provider 108, and client computing devices 110 operated by data subjects 112.

However, data security computing system 200 also includes at least one record integrator 202 communicatively coupled to a plurality of HCP data managers 204, which each store sensitive data (e.g., PII and/or PHI) in secure databases 206. HCP data managers 204 may be substantially similar to secure managers 104 shown and described with respect to FIG. 1, although operation of HCP data managers 204 may be governed in part by laws and/or regulations specific to the data security of PHI (e.g., HIPAA regulations, in the United States). As described above, HCP data managers 204 may store data in databases 206 according to disparate formats, and record integrator 202 is configured to provide unified and centralized access to the data managed by HCP data managers 204.

Service providers 102 are communicatively coupled to secure manager 104 and/or to record integrator(s) 202, to transmit access tokens thereto and to request and receive sensitive data from HCP data managers 204 via record integrator(s) 202. Record integrator(s) 202 are communicatively coupled to a network of HCP data managers 204 and manage data access therefrom. In some embodiments, secure manager 104 is communicatively coupled to HCP data managers 204 (i.e., without record integrator 202 as an intermediary) and may access/retrieve data therefrom. Service provider 102, secure manager 104, record integrator 202, and/or HCP data managers 204 may be communicatively coupled to token provider 108 to validate access tokens therewith, as described in greater detail herein.

Record integrator 202 and/or HCP data managers 204 may include any suitable computing device(s), such as one or more server computing device(s), cloud-based computing and/or storage systems, and/or any other device(s). HCP data managers 204 store sensitive data in databases 206, which are any suitable secure storage devices, including any suitable encryption and/or access restriction mechanisms.

Figure 3:
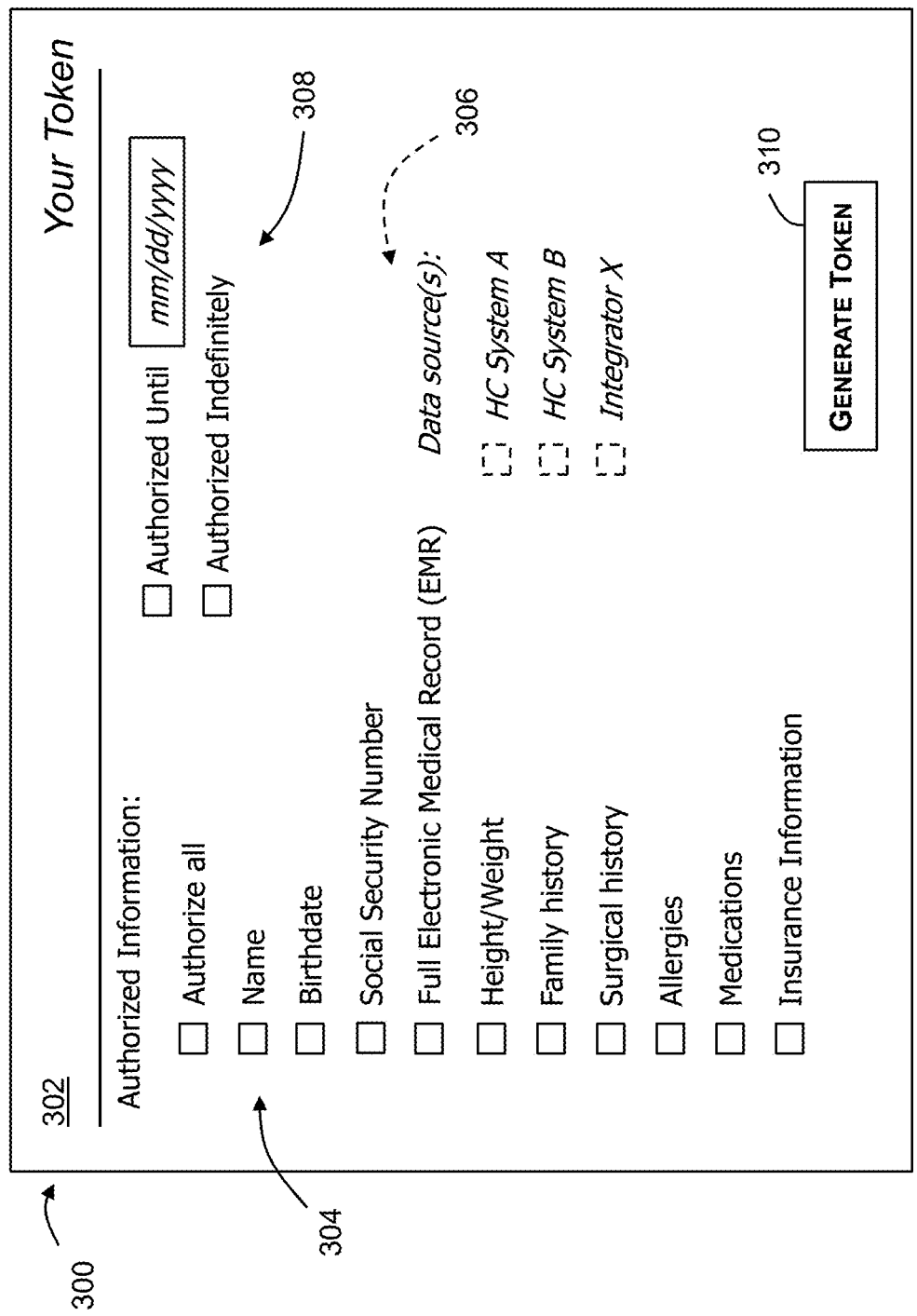

FIG. 3 illustrates one example token request environment 300, embodied as a website or user interface of a software app executed on client computing device 110 (shown in FIGS. 1 and 2). In some embodiments, data subject 112 (also shown in FIGS. 1 and 2) authenticates into the token request environment 300. For example, data subject 112 may provide a user name and password, a biometric identifier (e.g., a fingerprint or facial image), a PIN, a one-time PIN, and/or any other authentication information.

Data subject 112 navigates to the particular interface 302 shown in FIG. 3 by selecting a command to generate an access token. For example, as described elsewhere herein, data subject 112 may wish to provide PII and/or PHI to a service provider 102 (shown in FIGS. 1 and 2) without making their PII and/or PHI vulnerable to unauthorized access and without having to manually provide their PII and/or PHI (e.g., verbally, written, typed, etc.). As shown in interface 302, data subject 112 has provided or selected a plurality of data elements 304 of PII and/or PHI that are available to provide to service provider(s) 102 using an access token.

Data subject 112 selects one or more data elements 304 that data subject 112 wishes to provide to service provider 102. It should be understood that data subject 112 may not wish to provide all data elements 304 to a service provider 102, and may therefore select fewer than all available data elements 304. For example, it may not be necessary to provide a family history, surgical history, and medications to a service provider such as a dentist for a routine cleaning. In such an example, data subject 112 would not select those data elements 304.

Data subject 112 may also include additional authorization parameters. In one example embodiment, when data subject 112 selects certain data elements 304 of PHI, additional selectable elements 306 appear on interface 302. Selectable elements 306 are associated with data sources of PHI, such as disparate healthcare systems (e.g., HCP data managers 204, shown in FIG. 2) and/or one or more record integrators 202 (also shown in FIG. 2). Specifically, certain PHI such as medical records, surgical history, and the like may be maintained at disparate HCP data managers 204. Therefore, the access token must be generated to enable access to PHI from each of those HCP data managers 204. In certain embodiments, selecting a single record integrator 202 as a data source enables retrieval of all data elements 304 of PHI, such as where a single record integrator 202 serves all HCP data managers 204 that store the data subject's PHI.

Authorization parameters may additionally include validity or access restrictions 308, such as an authorization/validity date after which the service provider 102 is not authorized to access or store their data. Data subject 112 may select a specific date after which they wish to restrict or revoke access to their sensitive date, or may authorize such access indefinitely (e.g., until the data subject manually revokes an access token, or until a regulatory or statutory period of data retention expires). Although not shown, additional or alternative authorization parameters may be available for selection via interface 302, such as a selection of authorized service providers.

When data subject 112 is satisfied with their selection(s), data subject 112 selects a generation control 310, embodied here as a selectable button. Client computing device 110 generates an access token request message including a data definition of all selected data elements 304 and any authorization parameters selected and/or defined by data subject 112. Client computing device 110 transmits the access token request to token provider 108 (shown in FIG. 1).

Although not shown in FIG. 3, token request environment 300 may display additional and/or alternative interfaces. In particular, token request environment 300 may display, to data subject 112, an inventory of any/all access tokens that are active (e.g., still valid) and/or ever requested by the data subject 112. Data subject 112 may select any such access tokens for modification (e.g., to expand or contract the data available to service provider 102 via the access token, to extend or reduce the validity of the access token, etc.) or revocation.

FIGS. 4-9 are swim lane diagrams illustrating an example tokenized data access process 400 implemented using components of data security computing systems 100 and 200, shown in FIGS. 1 and 2. In the example embodiment, process 400 includes several stages, including a token generation stage 402 and a token usage stage 404.

Figure 4:
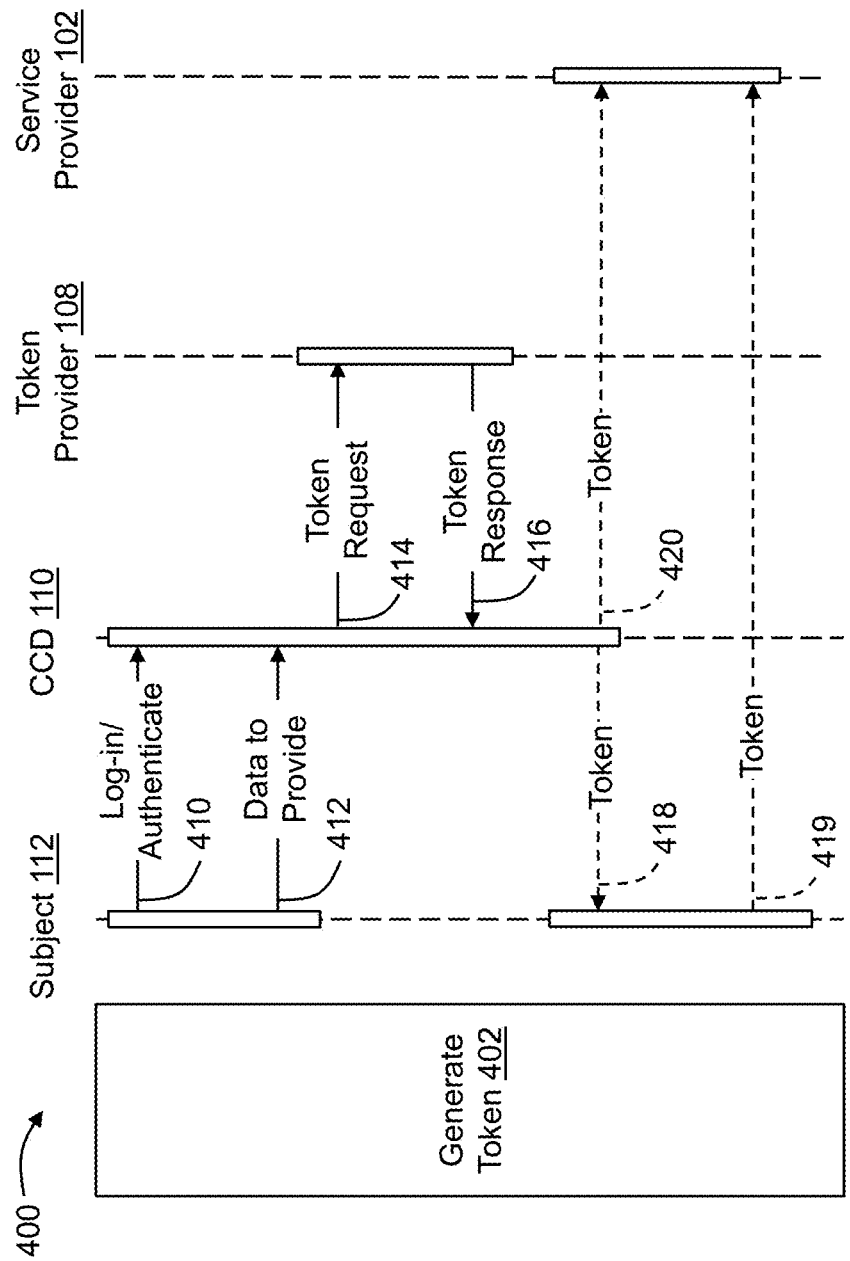

In token generation stage 402, as shown in FIG. 4, a user (e.g., data subject 112) logs in and/or authenticates into (410) a web browser and/or app environment on their client computing device 110, which may be maintained by token provider 108. As described herein, log-in/authentication (410) may include providing log-in/authentication credentials to client computing device 110, such as a username/password, PIN, biometric identifier (e.g., password, facial recognition, retinal scan, etc.), and the like. Thereafter, data subject 112 is authorized to interact with token provider 108 (via client computing device 110) to request and receive access tokens.

More specifically, data subject 112 selects information (412) that data subject 112 wishes to provide a service provider (e.g., a service provider 102) access to, via an access token. This selection step (412) may be implemented using an interface 302 as shown and described with respect to FIG. 3, and/or using any other web browser and/or app interface. Client computing device 110 generates and transmits (414) an access token request message, including the data definition and authorization parameters selected by the data subject 112, to token provider 108. Token provider 108 generates the access token as described herein, such as an alphanumeric code or computer-readable image content (e.g., a barcode or QR code).

Although not shown in FIG. 4, in some embodiments, token provider 108 authenticates data subject 112 prior to generating and/or providing the access token. For example, client computing device 110 may transmit (414) the log-in/authentication credentials entered by data subject 112 during the log-in/authentication step (410), or an indication of successful authentication, in the access token request message, and token provider 108 may use those credentials or indication to authenticate data subject 112. Additionally or alternatively, token provider 108 transmits an authentication request message back to client computing device 110 with instructions for client computing device 110 to request additional/alternative authentication credentials from data subject 112, which client computing device 110 returns to token provider 108 in an authentication response message.

Token provider 108 is configured to generate the access token according to data subject's data definition and authorization parameters, and to transmit (416) an access token response message, including the access token, back to client computing device 110. Although not shown in FIG. 4, token provider 108 also stores the access token in a secure memory location (e.g., an integral memory, a centralized token database, a non-centralized token database, etc.).

Client computing device 110 receives the access token from token provider 108. In some embodiments, client computing device 110 provides or displays (418) the access token to data subject 112. For example, where the access token is an alphanumeric code, client computing device 110 displays (418) the access code on a user interface thereof. Data subject 112 views the access token and provides (419) the access token to service provider 102 (e.g., by reading the access token to service provider 102 aloud, writing the access token, typing or pasting the access code into a fillable field, etc.). Additionally or alternatively, client computing device 110 transmits (420) the access token directly to service provider 102 (e.g., via NFC "tap" or other NFC communication, via SMS/text, via email, etc.).

Figure 5:
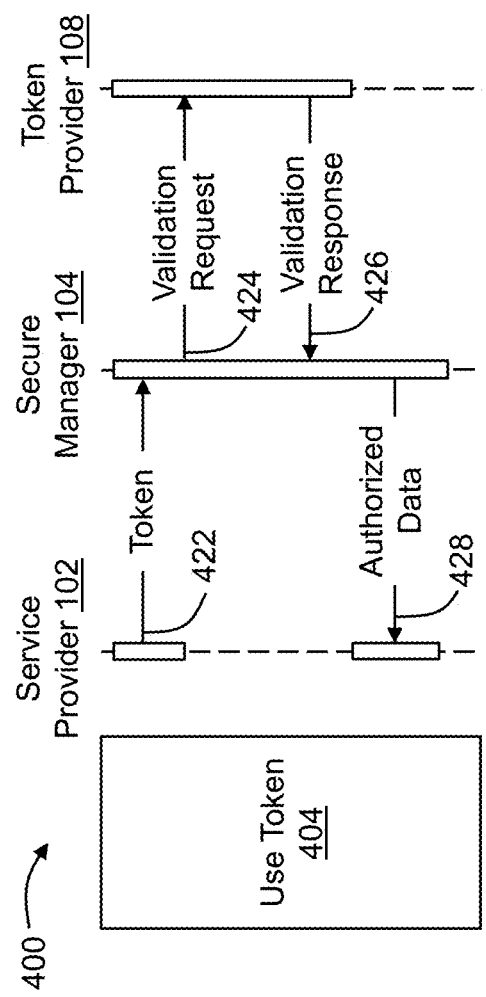

Once service provider 102 has received the access token, process 400 proceeds to token usage stage 404, various embodiments of which are shown in FIGS. 5-8. FIG. 5, specifically, illustrates token usage stage 404 implemented using data security computing system 100. Service provider 102 transmits (422) the access token to secure manager 104, or the source of the data that service provider 102 wishes to access. Service provider 102 transmits (422) the access token to secure manager 104 over any suitable communication channel. In some embodiments, service provider 102 also transmits a subject identifier, which may be received from data subject 112 (e.g., during provision 419) and/or from client computing device 110 (e.g., during transmission 420).

Secure manager 104 receives the access token, and transmits (424) the access token to token provider 108 in a token validation request message. Token provider 108 receives the access token from secure manager 104 and performs a lookup in the memory (e.g., database) to retrieve any matching stored access token. Where token provider 108 also receives a subject identifier, token provider 108 may use the subject identifier to perform the lookup operation, to retrieve active access tokens associated with data subject 112. Token provider 108 compares the received access token to the stored/retrieved access token, to determine if the access token is valid (e.g., is received from an authorized service provider 102, is within a validity date, is seeking data from the appropriate secure manager 104, etc.). Token provider 108 transmits (426) a token validation response message back to secure manager 104, the token validation response message indicating whether the access token was successfully validated. When the access token is successfully validated, the token validation response message may also include instructions that cause secure manager 104 to provide the requested data to service provider 102.

When the access token is successfully validated, secure manager 104 retrieves (e.g., from database(s) 106) the sensitive data (PII and/or PHI) that has been requested by service provider 102. Secure manager 104 transmits (428) the data back to service provider 102.

Although not shown in FIG. 5, in alternative embodiment, service provider 102 may communicate directly with token provider 108 to validate the access token prior to sending the access token to secure manager 104. In such embodiments, service provider 102 transmits the access token and/or an indication of successful validation of the access to secure manager 104. In response, secure manager 104 retrieves and transmits the requested and authorized data back to service provider 102.

Figure 6:
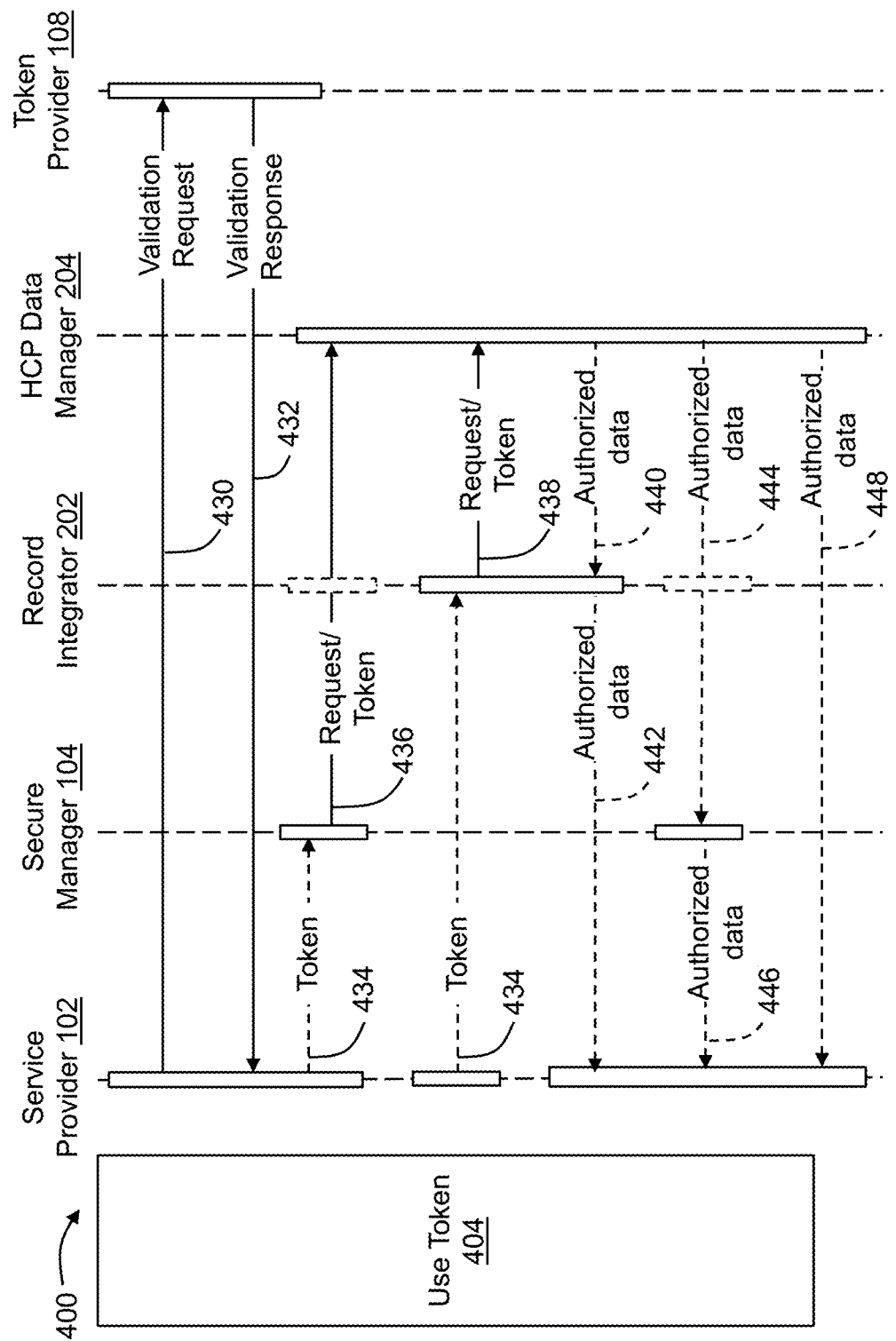
Figure 7:
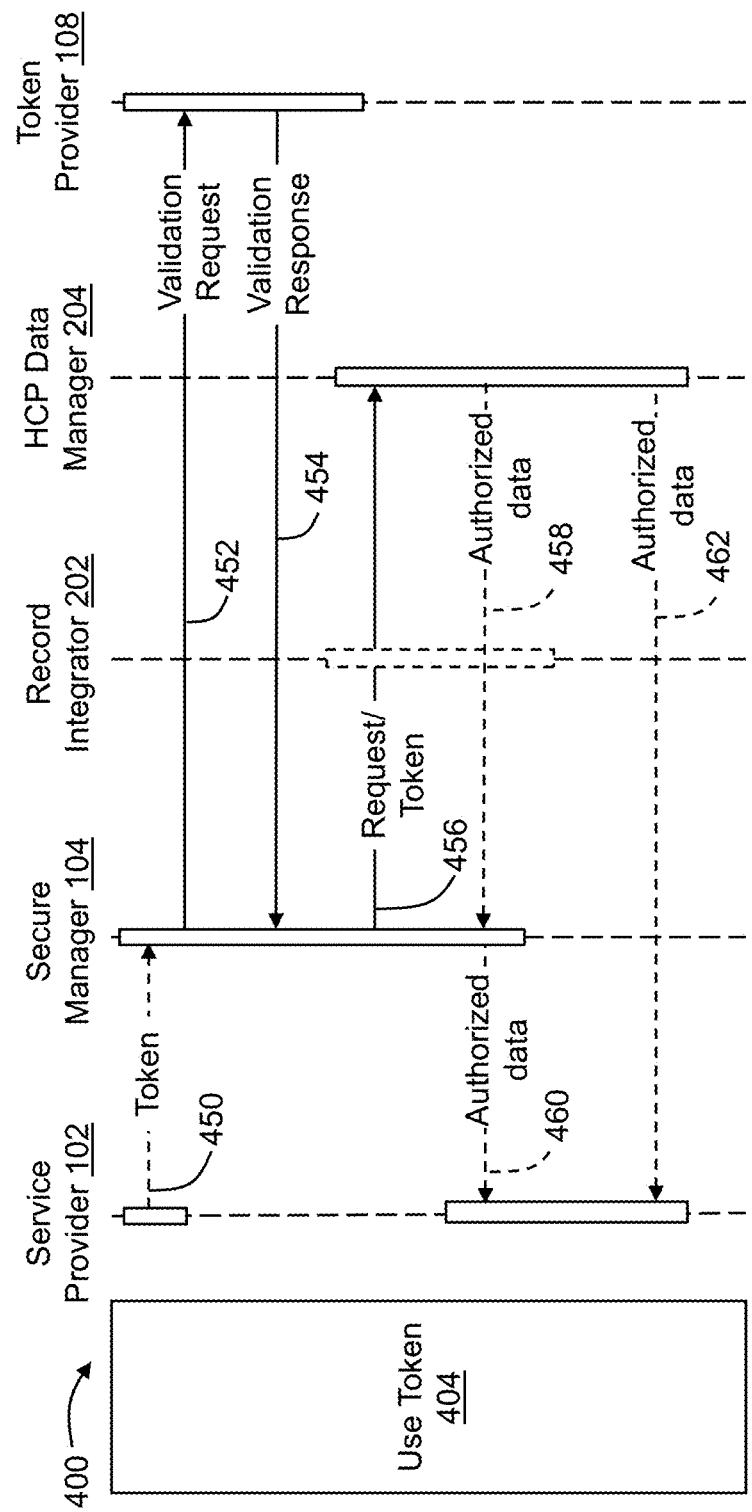
Figure 8:
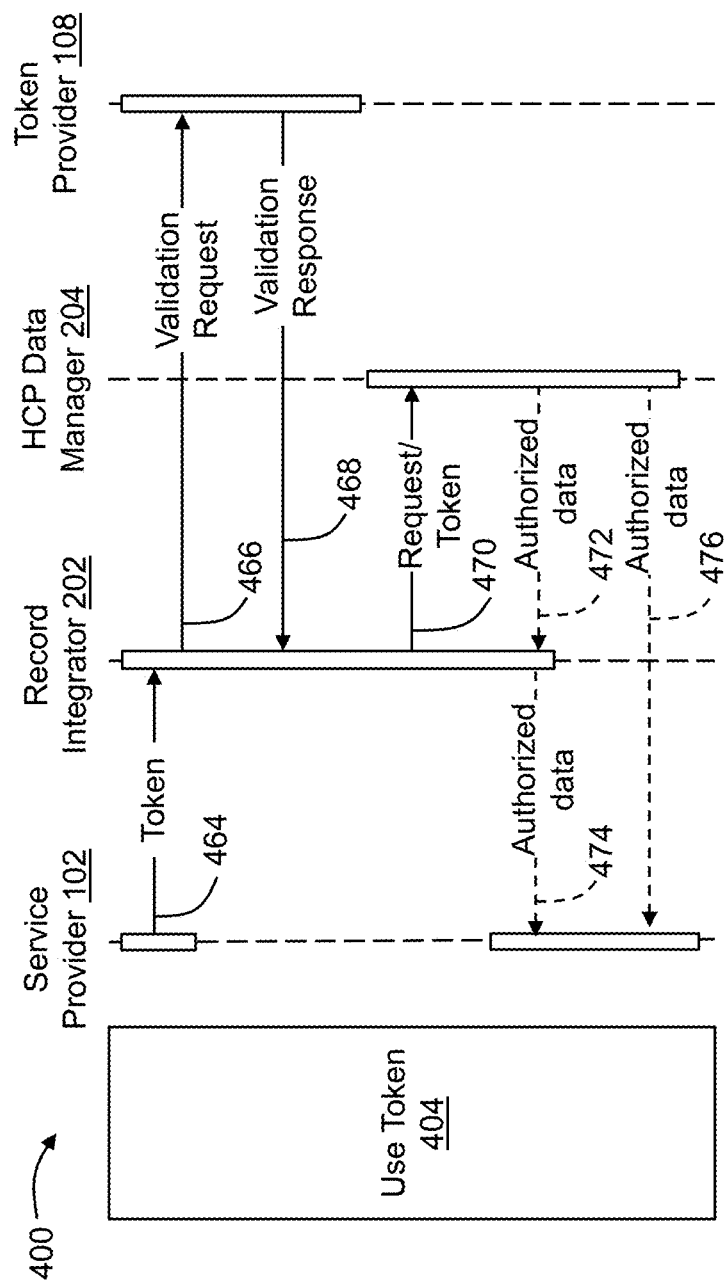

FIGS. 6-8 illustrate other embodiments of token usage stage 404 implemented using data security computing system 200.

In FIG. 6, service provider 102 has received the access token from data subject 112 and/or client computing device 110 thereof. In this embodiment, service provider 102 interacts directly with token provider 108 to validate the access token. Specifically, service provider 102 transmits (430) the received access token to token provider 108 for validation, in a token validation request message, as described above. Token provider 108 validates the received access token, as described above, and transmits (432) a token validation response message back to service provider 102.

Service provider 102 then transmits (434) the validated access token, along with an indicator that the access token has been successfully validated, to secure manager 104 or record integrator 202, requesting access to, specifically, PHI of data subject 112. Secure manager 104 or record integrator 202 receives the access token and the indication that the access token was successfully validated.

Where service provider 102 transmits (434) the validated access token to secure manager 104, secure manager 104 transmits (436) a request for the data identified by the access token to HCP data manager 204 (the particular HCP data manager 204 may also be identified by the access token), either directly or via record integrator 202. Alternatively, where service provider 102 transmits (434) the validated access token to record integrator 202, record integrator 202 then transmits (438) the request for the data identified by the access token to the HCP data manager 204. The request may include the validated access token and/or the indicator that the access token has been successfully validated.

HCP data manager 204 receives the request and/or the validated access token. In response, HCP data manager 204 retrieves (e.g., from database(s) 206) the data elements of PHI that data subject 112 requested to provide service provider 102 access to. HCP data manager 204 transmits (440) the requested and authorized PHI back to record integrator 202, which transmits (442) the requested and authorized PHI back to service provider 102. Alternatively, HCP data manager 204 transmits (444) the requested and authorized PHI back to secure manager 104, either directly or via record integrator 202, and secure manager 104 transmits (446) the requested and authorized PHI to service provider 102. Still alternatively, HCP data manager 204 transmits (448) the requested and authorized PHI directly to service provider 102.

In FIG. 7, service provider 102 has received the access token from data subject 112 and/or client computing device 110 thereof. In this embodiment, service provider 102 transmits (450) the access token to secure manager 104, and secure manager 104 interacts with token provider 108 to validate the access token. Specifically, secure manager 104 transmits (452) the received access token to token provider 108 for validation, in a token validation request message, as described above. Token provider 108 validates the received access token, as described above, and transmits (454) a token validation response message back to secure manager 104.

Secure manager 104 then transmits (456) a request for the data identified by the access token to HCP data manager 204 (the particular HCP data manager 204 may also be identified by the access token), either directly or via record integrator 202. The request may include the validated access token and/or an indicator that the access token has been successfully validated.

HCP data manager 204 receives the request and/or the validated access token. In response, HCP data manager 204 retrieves (e.g., from database(s) 206) the data elements of PHI that data subject 112 requested to provide service provider 102 access to. HCP data manager 204 transmits (458) the requested and authorized PHI back to secure manager 104, either directly or via record integrator 202. Secure manager 104 then transmits (460) the requested and authorized PHI back to service provider 102. Alternatively, HCP data manager 204 transmits (462) the requested and authorized PHI directly to service provider 102.

In FIG. 8, service provider 102 has received the access token from data subject 112 and/or client computing device 110 thereof. In this embodiment, service provider 102 transmits (464) the access token to record integrator 202, and record integrator 202 interacts with token provider 108 to validate the access token. Specifically, record integrator 202 transmits (466) the received access token to token provider 108 for validation, in a token validation request message, as described above. Token provider 108 validates the received access token, as described above, and transmits (468) a token validation response message back to record integrator 202.

Record integrator 202 then transmits (470) a request for the data identified by the access token to HCP data manager 204 (the particular HCP data manager 204 may also be identified by the access token). The request may include the validated access token and/or an indicator that the access token has been successfully validated. HCP data manager 204 receives the request and/or the validated access token. In response, HCP data manager 204 retrieves (e.g., from database(s) 206) the data elements of PHI that data subject 112 requested to provide service provider 102 access to. HCP data manager 204 transmits (472) the requested and authorized PHI back to record integrator 202, which transmits (474) the requested and authorized PHI back to service provider 102. Alternatively, HCP data manager 204 transmits (476) the requested and authorized PHI directly to service provider 102.

Figure 9:
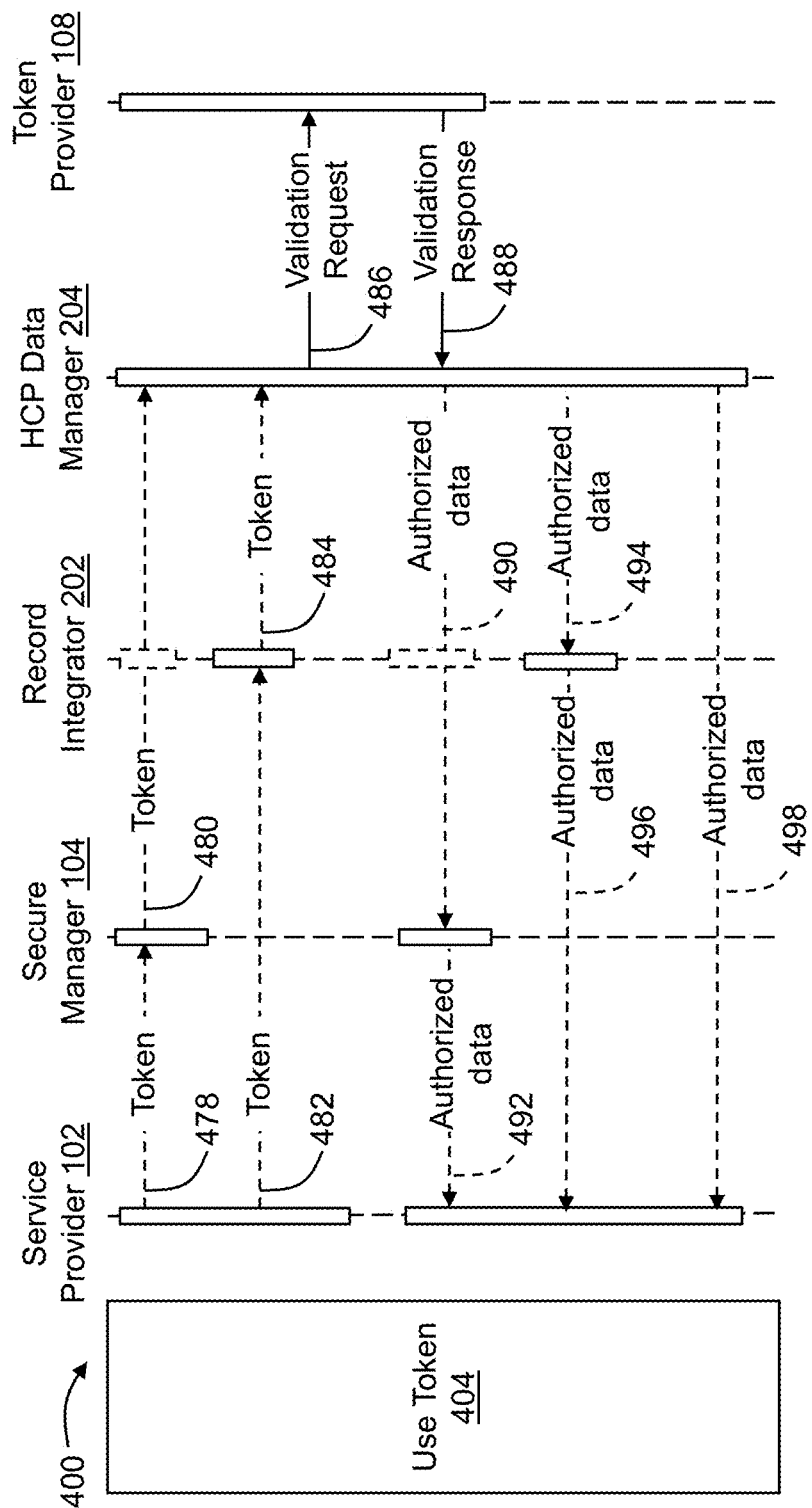

In FIG. 9, service provider 102 has received the access token from data subject 112 and/or client computing device 110 thereof. In this embodiment, service provider 102 transmits (478) the access token to secure manager 104, and secure manager 104 transmits (480) the access token to HCP data manager 204 (the particular HCP data manager 204 may also be identified by the access token), either directly or via record integrator 202. Alternatively, service provider 102 transmits (482) the access token to record integrator 202. Record integrator 202 transmits (484) the access token to HCP data manager 204 (the particular HCP data manager 204 may also be identified by the access token).

HCP data manager 204 interacts with token provider 108 to validate the access token. Specifically, HCP data manager 204 transmits (486) the received access token to token provider 108 for validation, in a token validation request message, as described above. Token provider 108 validates the received access token, as described above, and transmits (488) a token validation response message back to HCP data manager 204.

Upon successful validation of the access token, HCP data manager 204 retrieves (e.g., from database(s) 206) the data elements of PHI that data subject 112 requested to provide service provider 102 access to. HCP data manager 204 transmits (490) the requested and authorized PHI back to secure manager 104, either directly or via record integrator 202, and secure manager 104 transmits (492) the requested and authorized PHI back to service provider 102. Alternatively, HCP data manager 204 transmits (494) the request and authorized PHI back to record integrator 202, which transmits (496) the requested and authorized PHI back to service provider 102. Still alternatively, HCP data manager 204 transmits (498) the requested and authorized PHI directly to service provider 102.

Figure 10:
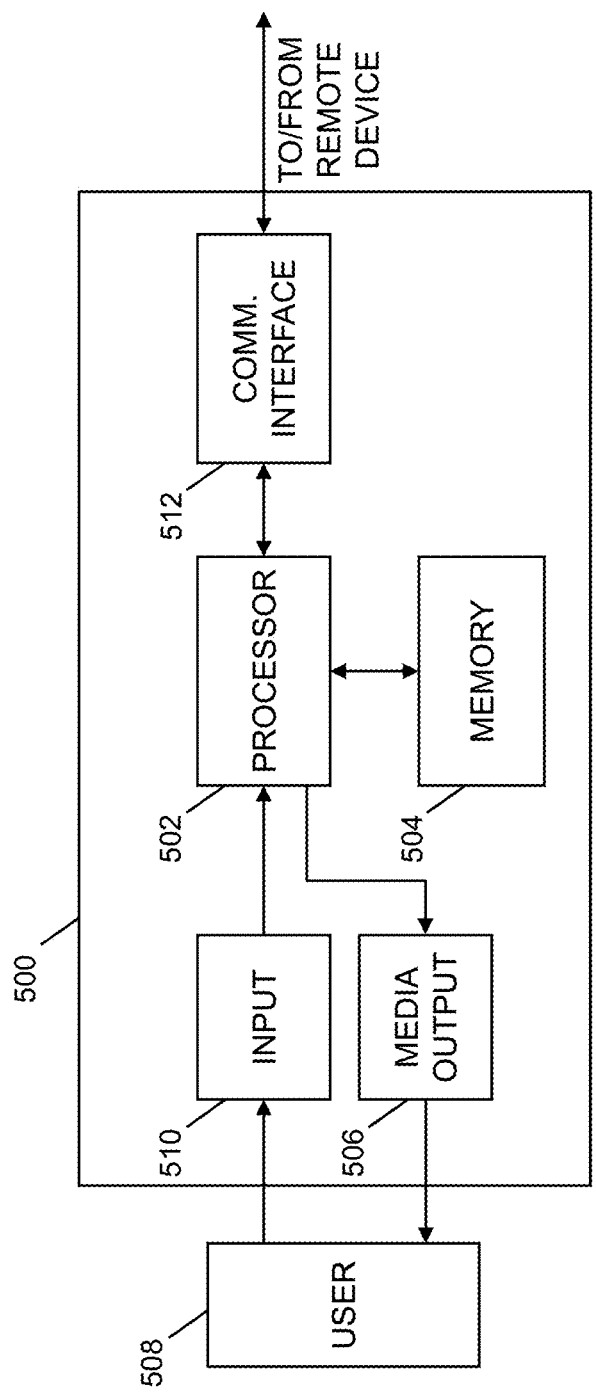

FIG. 10 illustrates an example configuration of a user system 500, such as client computing device 110 and/or a service provider computing device of service provider 102 (all shown in FIGS. 1 and 2). In the example embodiment, user system 500 includes a processor 502 for executing instructions. In some embodiments, executable instructions are stored in a memory area 504. Processor 502 may include one or more processing units, for example, a multi-core configuration. Memory area 504 is any device allowing information such as executable instructions to be stored and retrieved. Memory area 504 may include one or more computer readable media.

User system 500 also includes at least one media output component 506 for presenting information to a user 508 (e.g., data subject 112, shown in FIGS. 1 and 2). Media output component 506 is any component capable of conveying information to user 508. For example, media output component 506 may be a display component configured to display token request interface(s). In some embodiments, media output component 506 includes an output adapter such as a video adapter and/or an audio adapter. An output adapter is operatively coupled to processor 502 and operatively connectable to an output device such as a display device, a liquid crystal display (LCD), organic light emitting diode (OLED) display, or "electronic ink" display, or an audio output device, a speaker or headphones.

In some embodiments, user system 500 includes an input device 510 for receiving input from user 508. Input device 510 may include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output device of media output component 506 and input device 510.

Stored in memory area 504 are, for example, computer readable instructions for providing a user interface to user 508 via media output component 506 and receiving and processing input from input device 510. A user interface may include, among other possibilities, a web browser and client application ("app"). Web browsers enable users, such as user 508, to display and interact with media and other information typically embedded on a web page or a website.

Figure 11:
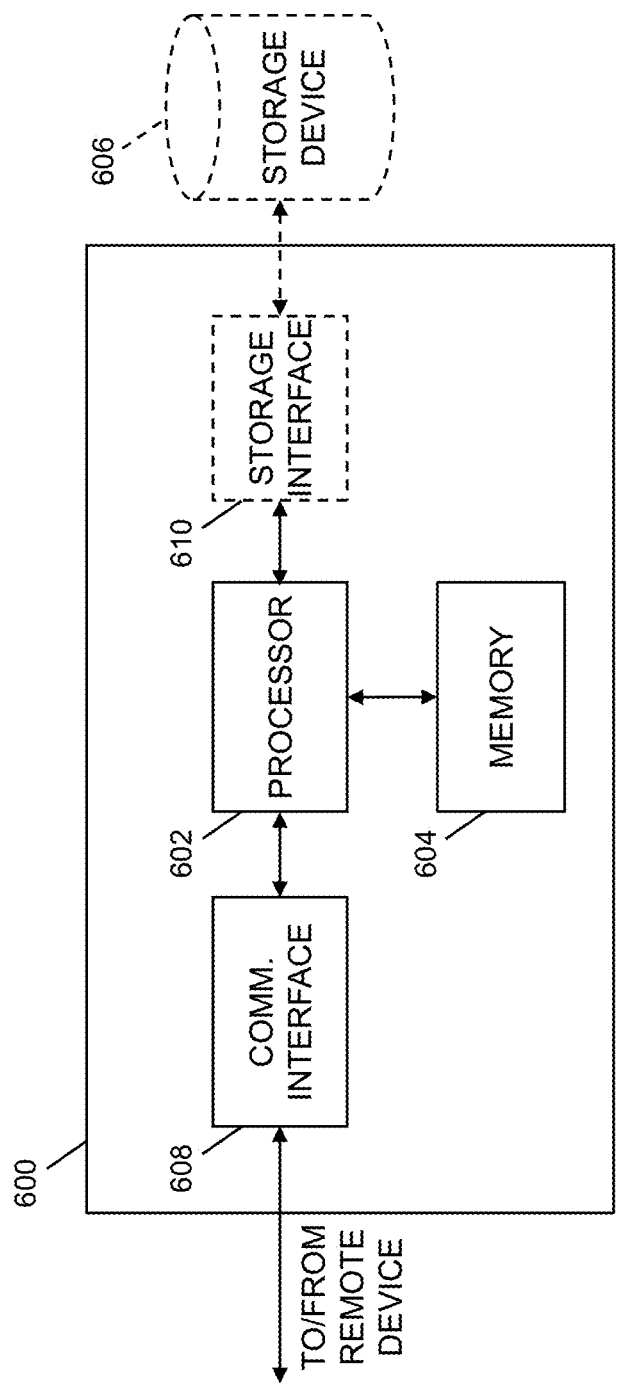

User system 500 may also include a communication interface 512, which is communicatively connectable to a remote device (e.g., a server system 600, shown in FIG. 11). Communication interface 512 may include, for example, a wired or wireless network adapter or a wireless data transceiver for use with a mobile phone network, Global System for Mobile communications (GSM), 3G, or other mobile data network or Worldwide Interoperability for Microwave Access (WIMAX).

FIG. 11 shows an example configuration of a server system 600. Server system 600 may include, but is not limited to, token provider 108, secure manager 104 (both shown in FIG. 1), record integrator 202, HCP data managers 204 (both shown in FIG. 2), and/or computing device(s) associated with any party to data security computing systems 100 and 200 (respectively shown in FIGS. 1 and 2).

Server system 600 includes a processor 602 for executing instructions. Instructions may be stored in a memory area 604, for example. Processor 602 may include one or more processing units (e.g., in a multi-core configuration) for executing instructions. The instructions may be executed within a variety of different operating systems on server system 600, such as UNIX, LINUX, Microsoft Windows®, etc. More specifically, the instructions may cause various data manipulations on data stored in memory 604 and/or in a storage device 606 (e.g., create, read, update, and delete procedures). It should also be appreciated that upon initiation of a computer-based method, various instructions may be executed during initialization. Some operations may be required in order to perform one or more processes described herein, while other operations may be more general and/or specific to a particular programming language (e.g., C, C #, C++, Java, or other suitable programming languages, etc.).

Processor 602 is operatively coupled to a communication interface 608 such that server system 600 is capable of communicating with a remote device such as a user system 500 (shown in FIG. 10) or another server system 600. Processor 602 may also be operatively coupled to storage device 606. Storage device 606 is any computer-operated hardware suitable for storing and/or retrieving data. In some embodiments, storage device 606 is integrated in server system 600. In other embodiments, storage device 606 is external to server system 600. For example, server system 600 may include one or more hard disk drives as storage device 606. In other embodiments, storage device 606 is external to server system 600 and may be accessed by a plurality of server systems 600. For example, storage device 606 may include multiple storage units such as hard disks or solid state disks in a redundant array of inexpensive disks (RAID) configuration. Storage device 606 may include a storage area network (SAN) and/or a network attached storage (NAS) system.

In some embodiments, processor 602 is operatively coupled to storage device 606 via a storage interface 610. Storage interface 610 is any component capable of providing processor 602 with access to storage device 606. Storage interface 610 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 602 with access to storage device 606.

Memory area 604 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are exemplary only, and are thus not limiting as to the types of memory usable for storage of a computer program.

Figure 12:
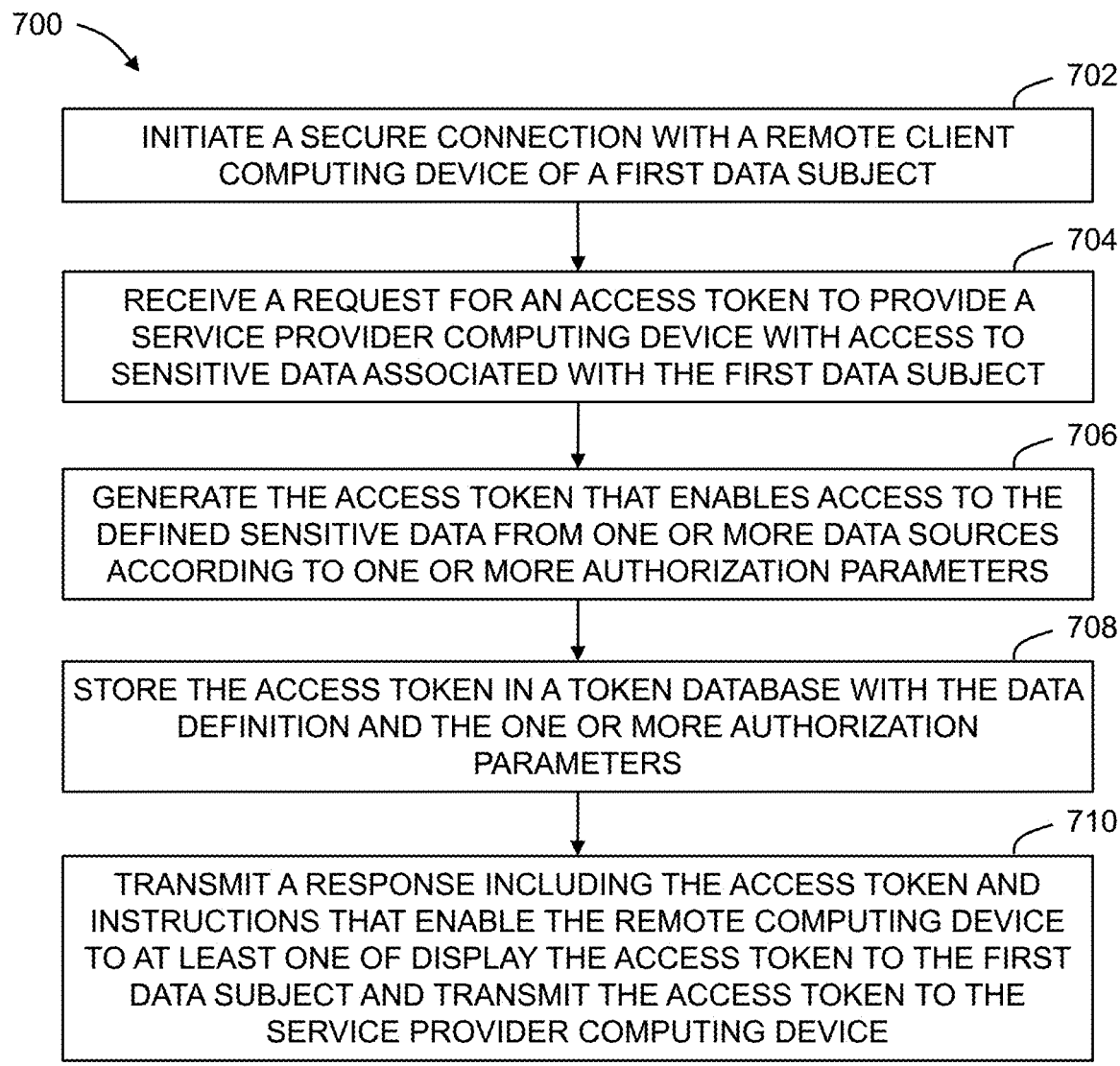

FIG. 12 is an example flow diagram illustrating a method 700 for enabling tokenized access to sensitive user data (e.g., PII and/or PHI). Method 700 may be implemented using one or more components of data security computing system 100 (shown in FIG. 1) and/or data security computing system 200 (shown in FIG. 2). Specifically, method 700 is implemented using token provider 108 (shown in FIGS. 1 and 2).

Method 700 includes initiating 702 a secure connection with a remote client computing device (e.g., client computing device 110) of a first data subject (e.g., data subject 112, both shown in FIGS. 1 and 2), and receiving 704, from the remote client computing device of the first data subject, a request for an access token to provide a service provider computing device (e.g., service provider 102, also shown in FIGS. 1 and 2) with access to sensitive data associated with the first data subject. The request includes a data definition of the sensitive data to which access is to be provided and one or more authorization parameters including one or more data source identifiers of a respective one or more data sources (e.g., HCP data managers 204, shown in FIG. 2) at which the defined sensitive data is stored.

Method 700 also includes generating 706 the access token that enables access to the defined sensitive data from the one or more data sources according to the one or more authorization parameters, and storing 708 the access token in a token database with the data definition and the one or more authorization parameters. Method 700 further includes transmitting 710, to the remote client computing device of the first data subject, a response including the access token and instructions that enable the remote computing device to of display the access token to the first data subject or transmit the access token to the service provider computing device.

Method 700 may include additional, fewer, and/or alternative steps. For example, in some embodiments, method 700 further includes authenticating the request for the access token. In some such embodiments, the request for the access token further includes authentication credentials input by the first data subject to the remote client computing device during a log-in process, and the authenticating includes processing the authentication credentials received from the remote client computing device. In other such embodiments, the authenticating includes transmitting an authentication request message to the remote client computing device, the authentication request message including instructions that cause the remote client computing device to prompt the first data subject to input one or more authentication credentials into the remote client computing device, receiving, from the remote client computing device, an authentication response message including the one or more input authentication credentials, and processing the input authentication credentials.

In some embodiments, method 700 further includes receiving a token validation request message from the service provider computing device, the token validation request message including the access token and a subject identifier associated with the data subject, performing a lookup operation using at least one of the access token or the subject identifier, validating the access token when the lookup operation returns a valid and active stored access token, and transmitting a token validation response message to the service provider computing device, the token validation response message including an indication that the access token was successfully validated.

In certain embodiments, method 700 further includes receiving a token validation request message from a record integrator associated with a healthcare provider (HCP) data manager that stores the sensitive data to which access is to be provided and that is identified by the data source authorization parameter, the token validation request message including the access token and a subject identifier associated with the data subject, performing a lookup operation using at least one of the access token or the subject identifier, validating the access token when the lookup operation returns a valid and active stored access token, and transmitting a token validation response message to the record integrator, the token validation response message including an indication that the access token was successfully validated.

In still other embodiments, method 700 includes receiving a token validation request message from a healthcare provider (HCP) data manager that stores the sensitive data to which access is to be provided and that is identified by the data source authorization parameter, the token validation request message including the access token and a subject identifier associated with the data subject, performing a lookup operation using at least one of the access token or the subject identifier, validating the access token when the lookup operation returns a valid and active stored access token, and transmitting a token validation response message to the HCP data manager, the token validation response message including an indication that the access token was successfully validated. In some such embodiments, the token validation response message further includes instructions that cause the HCP data manager to transmit the sensitive data to the service provider computing device.

In some embodiments, method 700 further includes receiving, from the remote client computing device, data subject input indicating a revocation of the access token, and in response to receiving the data subject input, deleting the stored access token or disabling the stored access token to prevent further access to the sensitive data by the service provider computing device.

In still further embodiments, the one or more authorization parameters include a validity date after which access to the sensitive data is revoked, and method 700 also includes, upon reaching the validity date, deleting the stored access token or disabling the stored access token to prevent further access to the sensitive data by the service provider computing device.

As will be appreciated based on the foregoing specification, the above-described embodiments of the disclosure may be implemented using computer programming or engineering techniques including computer software, firmware, hardware or any combination or subset thereof, wherein the technical effect is to enable the use of access tokens to maintain security of PII and/or PHI while authorizing access to such data by one or more service providers. Any such resulting program, having computer-readable code means, may be embodied or provided within one or more computer-readable media, thereby making a computer program product, (i.e., an article of manufacture), according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A data security system for enabling tokenized access to sensitive data, the data security system comprising a token provisioning computing device including at least one processor communicatively coupled to a memory device, the at least one processor configured to:
   receive, from a remote client computing device of a data subject, a request for an access token to provide a service provider computing device with access to the sensitive data associated with the data subject, wherein the request includes one or more authorization parameters including one or more data identifiers each for identifying a data element included in a set of the sensitive data accessible to the service provider computing device;
   generate (i) a first access token that enables access to a first subset of sensitive data included in the set of sensitive data according to the one or more authorization parameters, and (ii) a second access token that enables access to a second subset of sensitive data included in the set of sensitive data according to the one or more authorization parameters;
   store the first and second access tokens in a token database with the one or more corresponding authorization parameters;
   receive, from the service provider computing device, a first data access request including a first candidate access token;
   identify the first subset of sensitive data accessible to the service provider computing device by matching the first candidate access token to the stored first access token; and
   transmit the first subset of sensitive data to the service provider computing device.

2. The data security system of claim 1, wherein the at least one processor is further configured to:
   cause to display, on the remote client computing device, a user interface including the one or more authorization parameters, the one or more authorization parameters selectable by the data subject via the user interface.

3. The data security system of claim 2, wherein one of the one or more authorization parameters include a predefined time the service provider computing device is authorized to access the set of sensitive data.

4. The data security system of claim 1, wherein the at least one processor is further configured to initiate a secure connection with the remote client computing device prior to receiving the request for the access token.

5. The data security system of claim 1, wherein the request further includes a data definition of the set of sensitive data to which access is to be provided, and wherein one or more access tokens are generated to enable access to the defined set of sensitive data.

6. The data security system of claim 1, wherein the at least one processor is further configured to:
   generate the second access token subsequent to the generation of the first access token, wherein the second access token is generated after the first access token expires; and
   transmit, to the remote client computing device, at least one response including the first and second access tokens and instructions that enable the remote client computing device to at least one of display the first and second access tokens to the data subject or transmit the first and second access tokens to the service provider computing device.

7. The data security system of claim 1, wherein the at least one processor is further configured to:
   receive, from the service provider computing device, a second data access request including a second candidate access token;
   identify the second subset of sensitive data accessible to the service provider computing device by matching the second candidate access token to the stored second access token; and transmit the second subset of sensitive data to the service provider computing device, wherein a portion of the second subset of sensitive data is either different from or the same as a portion of the first subset of sensitive data.

8. A computer-implemented method for enabling tokenized access to sensitive data, the method implemented using a data security system including a token provisioning computing device including at least one processor communicatively coupled to a memory device, the method comprising:
receiving, from a remote client computing device of a data subject, a request for an access token to provide a service provider computing device with access to the sensitive data associated with the data subject, wherein the request includes one or more authorization parameters including one or more data identifiers each for identifying a data element included in a set of the sensitive data accessible to the service provider computing device;
generating (i) a first access token that enables access to a first subset of sensitive data included in the set of sensitive data according to the one or more authorization parameters, and (ii) a second access token that enables access to a second subset of sensitive data included in the set of sensitive data according to the one or more authorization parameters;
storing the first and second access tokens in a token database with the one or more corresponding authorization parameters;
receiving, from the service provider computing device, a first data access request including a first candidate access token;
identifying the first subset of sensitive data accessible to the service provider computing device by matching the first candidate access token to the stored first access token; and
transmitting the first subset of sensitive data to the service provider computing device.

9. The computer-implemented method of claim 8 further comprising:
causing to display, on the remote client computing device, a user interface including the one or more authorization parameters, the one or more authorization parameters selectable by the data subject via the user interface.

10. The computer-implemented method of claim 9, wherein one of the one or more authorization parameters includes a predefined time the service provider computing device is authorized to access the set of sensitive data.

11. The computer-implemented method of claim 8 further comprising initiating a secure connection with the remote client computing device prior to receiving the request for the access token.

12. The computer-implemented method of claim 8, wherein the request further includes a data definition of the set of sensitive data to which access is to be provided, and wherein the first and second access tokens are generated to enable access to the defined set of sensitive data.

13. The computer-implemented method of claim 8 wherein receiving, from a remote client computing device of a data subject, a request for an access token further comprises receiving, from the remote computing device of the data subject, a request for one or more access tokens for providing to one or more service providers to access the sensitive data associated with the data subject, and the method further comprising:
generating the first token for a first service provider and the second access token for a second service provider; and
transmitting, to the remote client computing device, a response including the first and second access tokens and instructions that enable the remote client computing device to at least one of display the first and second access tokens to the data subject or transmit the first access token to the first service provider computing device and the second access token to the second service provider computing device.

14. The computer-implemented method of claim 8 further comprising:
receiving, from the service provider computing device, a second data access request including a second candidate access token;
identifying the second subset of sensitive data accessible to the service provider computing device by matching the second candidate access token to the stored second access token; and
transmitting the second subset of sensitive data to the service provider computing device, wherein a portion of the second subset of sensitive data is either different from or the same as a portion of the first subset of sensitive data.

15. At least one non-transitory computer-readable storage medium having computer-executable instructions stored thereon, wherein when executed by at least one processor of a token provisioning computing device of a data security computing system, the computer-executable instructions cause the at least one processor to:
receive, from a remote client computing device of a data subject, a request for an access token to provide a service provider computing device with access to sensitive data associated with the data subject, wherein the request includes one or more authorization parameters including one or more data identifiers each for identifying a data element included in a set of the sensitive data accessible to the service provider computing device;
generate (i) a first access token that enables access to a first subset of sensitive data included in the set of sensitive data according to the one or more authorization parameters, and (ii) a second access token that enables access to a second subset of sensitive data included in the set of sensitive data according to the one or more authorization parameters;
store the first and second access tokens in a token database with the one or more corresponding authorization parameters;
receive, from the service provider computing device, a first data access request including a first candidate access token;
identify the first subset of sensitive data accessible to the service provider computing device by matching the first candidate access token to the stored first access token; and
transmit the first subset of sensitive data to the service provider computing device.

16. The non-transitory computer-readable storage medium of claim 15, wherein the computer-executable instructions further cause the at least one processor to:
cause to display, on the remote client computing device, a user interface including the one or more authorization parameters, the one or more authorization parameters selectable by the data subject via the user interface.

17. The non-transitory computer-readable storage medium of claim 15, wherein the computer-executable instructions further cause the at least one processor to initiate a secure connection with the remote client computing device prior to receiving the request for the access token.

18. The non-transitory computer-readable storage medium of claim 15, wherein the request further includes a data definition of the set of sensitive data to which access is to be provided, and wherein the first and second access tokens are generated to enable access to the defined set of sensitive data.

19. The non-transitory computer-readable storage medium of claim 15, wherein the computer-executable instructions further cause the at least one processor to:
generate the second access token subsequent to the generation of the first access token, wherein the second access token is generated after the first access token expires; and
transmit, to the remote client computing device, at least one response including the first and second access tokens and instructions that enable the remote client computing device to at least one of display the first and second access tokens to the data subject or transmit the first and second access tokens to the service provider computing device.

20. The non-transitory computer-readable storage medium of claim 15, wherein the computer-executable instructions further cause the at least one processor to:
receive, from the service provider computing device, a second data access request including a second candidate access token;
identify the second subset of sensitive data accessible to the service provider computing device by matching the second candidate access token to the stored second access token; and
transmit the second subset of sensitive data to the service provider computing device, wherein a portion of the second subset of sensitive data is either different from or the same as a portion of the first subset of sensitive data.

* * * * *